(12) United States Patent
Zhao et al.

(10) Patent No.: US 12,733,861 B2
(45) Date of Patent: Sep. 15, 2026

(54) MULTIMODAL BRAIN FUNCTION SIGNAL ACQUISITION DEVICE AND METHOD

(71) Applicant: KINGFAR INTERNATIONAL INC., Beijing (CN)

(72) Inventors: Qichao Zhao, Beijing (CN); Ran Yang, Beijing (CN); Zhao Li, Beijing (CN)

(73) Assignee: KINGFAR INTERNATIONAL INC., Beijing (CN)

( * ) Notice: Subject to any disclaimer, the term of this patent is extended or adjusted under 35 U.S.C. 154(b) by 398 days.

(21) Appl. No.: 18/504,543

(22) Filed: Nov. 8, 2023

(65) Prior Publication Data

US 2024/0215902 A1 Jul. 4, 2024

(30) Foreign Application Priority Data

Dec. 30, 2022 (CN) ......................... 202211726776.2
Dec. 30, 2022 (CN) ......................... 202211726822.9

(51) Int. Cl.
*A61B 5/384* (2021.01)
*A61B 5/00* (2006.01)
(Continued)

(52) U.S. Cl.
CPC .......... *A61B 5/384* (2021.01); *A61B 5/14553* (2013.01); *A61B 5/256* (2021.01);
(Continued)

(58) Field of Classification Search
CPC ..... A61B 5/384; A61B 5/14553; A61B 5/256; A61B 5/259; A61B 5/265; A61B 5/291;
(Continued)

(56) References Cited

U.S. PATENT DOCUMENTS 5,987,351 A * 11/1999 Chance .............. A61B 5/14552 600/476
2017/0172447 A1* 6/2017 Mitra .................. A61B 5/0075
(Continued)

FOREIGN PATENT DOCUMENTS

CN 201840480 5/2011
CN 102156541 8/2011
(Continued)

OTHER PUBLICATIONS

Extended European Search Report, issued in the corresponding European patent application No. 23208600.9, dated Mar. 27, 2024, 4 pages.

(Continued)

*Primary Examiner* — Brian L Casler
(74) *Attorney, Agent, or Firm* — HSML P.C.

(57) ABSTRACT

A multimodal brain function signal acquisition device and method are provided. The device comprises: a cap; an electroencephalogram (EEG) signal acquisition device which comprises a support member and a plurality of acquisition tentacles; the support member is a hollow cylinder, the acquisition tentacles are disposed along a circumference of a first port of the support member, and the first port is connected to the cap; a near-red signal acquisition device which comprises a light guide column, a near infrared light source and a photodiode; the light guide column is a transparent hollow cylinder disposed within an inner periphery of the support member, the near infrared light source and the photodiode are disposed at a second port of the light guide column, and the first port of the light guide column is fixed on the cap; a transimpedance amplifier connected to the photodiode; a first analog-to-digital converter connected to the EEG signal acquisition device; a second analog-to-digital converter connected to the photodiode; and a microcontrol unit connected to the first analog-to-digital converter and the second analog-to-digital converter.

20 Claims, 10 Drawing Sheets

(51) Int. Cl.

| | |
|---|---|
| ***A61B 5/1455*** | (2006.01) |
| ***A61B 5/256*** | (2021.01) |
| ***A61B 5/259*** | (2021.01) |
| ***A61B 5/265*** | (2021.01) |
| ***A61B 5/291*** | (2021.01) |
| ***A61B 5/31*** | (2021.01) |

(52) U.S. Cl.
CPC .............. *A61B 5/259* (2021.01); *A61B 5/265* (2021.01); *A61B 5/291* (2021.01); *A61B 5/31* (2021.01); *A61B 5/7225* (2013.01); *A61B 5/7271* (2013.01); *A61B 2560/02* (2013.01); *A61B 2560/0468* (2013.01); *A61B 2562/0215* (2017.08); *A61B 2562/0238* (2013.01); *A61B 2562/043* (2013.01); *A61B 2562/227* (2013.01)

(58) Field of Classification Search
CPC ....... A61B 5/31; A61B 5/7225; A61B 5/7271; A61B 2560/02; A61B 2560/0468; A61B 2562/0215; A61B 2562/0238; A61B 2562/043; A61B 2562/227; A61B 5/0075; A61B 5/0082; A61B 5/4064; A61B 5/6803; A61B 5/6814; A61B 5/25; A61B 5/251; A61B 5/369; A61B 5/0059
USPC .......................................................... 600/544
See application file for complete search history.

(56) References Cited

U.S. PATENT DOCUMENTS

| | | | | |
|---|---|---|---|---|
| 2017/0281014 | A1* | 10/2017 | von Luehmann .. | A61B 5/14551 |
| 2017/0290524 | A1 | 10/2017 | Jiang et al. | |
| 2019/0307352 | A1* | 10/2019 | Li ...................... | A61B 5/14553 |

FOREIGN PATENT DOCUMENTS

| | | | |
|---|---|---|---|
| CN | 104146707 | 11/2014 | |
| CN | 104363983 | 2/2015 | |
| CN | 106037667 | 10/2016 | |
| CN | 106236079 | 12/2016 | |
| CN | 106618599 | 5/2017 | |
| CN | 209404778 | 9/2019 | |
| CN | 112754497 | 5/2021 | |
| CN | 113520407 | 10/2021 | |
| CN | 216210567 | 4/2022 | |
| CN | 115054242 | 9/2022 | |
| FR | 2899089 | 10/2007 | |
| KR | 20120002490 | 4/2012 | |
| KR | 20140089973 | 7/2014 | |
| KR | 20160081846 | 7/2016 | |
| WO | WO-2019000088 A1 * | 1/2019 | ............... A61B 5/30 |

OTHER PUBLICATIONS

Chinese First Office Action and Search Report, issued in the corresponding Chinese patent application No. 202211726822.9, dated May 15, 2024, 21 pages with the machine translation.

Xu et al., "A 665 μW Silicon Photomultiplier-Based NIRS/EEG/EIT Monitoring ASIC for Wearable Functional Brain Imaging", IEEE Transactions on Biomedical Circuits and Systems, vol. 12, No. 6, Dec. 2018, 5 pages.

First Office Action and Search Report, issued in the corresponding Chinese patent application No. 202211726776.2, dated May 18, 2025, 24 pages with the English translation.

Second Office Action, issued in the corresponding Chinese patent application number No. 202211726776.2, dated Jul. 26, 2025, 19 pages with the English translation.

* cited by examiner

MULTIMODAL BRAIN FUNCTION SIGNAL ACQUISITION DEVICE AND METHOD

This application claims priorities to Chinese Patent Application No. CN202211726822.9, filed on Dec. 30, 2022, and Chinese Patent Application No. CN202211726776.2, filed on Dec. 30, 2022, which is hereby incorporated by reference in its entirety.

TECHNICAL FIELD

The present disclosure relates to the technical field of brain function detections, and particularly to a multimodal brain function signal acquisition device and method.

BACKGROUND

The multimodal synchronous monitoring of the brain state is widely used in brain function researches. In the multimodal monitoring, the combination of a functional near infrared spectroscopy (FNIRS) and an electroencephalogram (EEG) has attracted more and more attention. However, in the prior art, during brain monitoring, an FNIRS detection device and an EEG detection device can only be placed adjacent to each other to monitor the activity state of a brain part separately rather than simultaneously. Using one monitoring technology to monitor a user's brain activities simultaneously will lead to the problem of inaccurate monitoring.

SUMMARY

In view of this, the embodiments of the present disclosure provide a multimodal brain function signal acquisition device and method, so as to solve the problem that in the prior art, a same brain part cannot be simultaneously and accurately monitored by a functional near infrared spectroscopy (FNIRS) and an electroencephalogram (EEG).

An aspect of the present disclosure provides a multimodal brain function signal acquisition device, comprising:

a cap;

an electroencephalogram (EEG) signal acquisition device which comprises a support member and a plurality of acquisition tentacles; the support member is a hollow cylinder, the acquisition tentacles are disposed along a circumference of a first end of the support member, and the first end is connected to the cap; the acquisition tentacles are in contact with a user's scalp to acquire the user's EEG signal;

a near-red signal acquisition device which comprises a light guide column, a near infrared light source and a photodiode; the light guide column is a transparent hollow cylinder with a diameter smaller than that of the support member; the light guide column is disposed within an inner periphery of the support member, the near infrared light source and the photodiode are disposed at a second port of the light guide column, and the first port of the light guide column is fixed on the cap; after near infrared light emitted by the near infrared light source arrives at the user's cerebral cortex through the light guide column and the near infrared light with a specific wavelength is absorbed by oxyhemoglobin and deoxyhemoglobin in the user's cerebral cortex, the photodiode receives the unabsorbed near infrared light which is scattered and arrives at the photodiode through the light guide column, and converts the unabsorbed near infrared light into a current signal, so as to obtain the changes of oxyhemoglobin and deoxyhemoglobin in the user's brain by analyzing the current signal, thereby obtain the motion situation of the user's brain;

a transimpedance amplifier connected to the photodiode and configured to convert the current signal into an analog voltage signal;

a first analog-to-digital converter connected to the EEG signal acquisition device and configured to convert the EEG signal into a first digital signal;

a second analog-to-digital converter connected to the transimpedance amplifier and configured to convert the analog voltage signal into a second digital signal; and a micro-control unit connected to the first analog-to-digital converter and the second analog-to-digital converter, and configured to receive the first digital signal output by the first analog-to-digital converter and the second digital signal output by the second analog-to-digital converter.

In some embodiments, the support member and each of the acquisition tentacles are made of silver chloride.

In some embodiments, during the acquisition of the EEG signal, each of the acquisition tentacles is coated with conductive gel.

In some embodiments, the light guide column is made of acrylic resin, epoxy resin, glass or polycarbonate.

In some embodiments, an inner wall of the light guide column is coated with reflective coating.

In some embodiments, the multimodal brain function signal acquisition device further comprises an analog circuit configured to perform high-pass filtering, low-pass filtering and signal amplitude amplification processing on the EEG signal acquired by the EEG signal acquisition device, and the processed signal is input into the first analog-digital converter; and a second-order low-pass filter circuit configured to perform low-pass filtering on the voltage signal output by the transimpedance amplifier, and the low-pass filtered voltage signal is input into the second analog-digital converter.

In some embodiments, the EEG signal acquisition device further comprises:

an acquisition electrode module configured to acquire an electrical signal of a brain area based on the plurality of acquisition tentacles as acquisition electrodes, the acquisition electrode module comprising two first amplifiers U2 and a second amplifier U1, wherein an input end of one of the first amplifiers U2 is configured to access the electrical signal acquired by the acquisition electrode, and an input end of the second amplifier U1 is connected to an output end of the first amplifier U2 accessing the acquired electrical signal; an input end of the other of the first amplifiers U2 is connected to an output end of the second amplifier U1, and an output end of the other of the first amplifiers U2 is connected to the input end of the second amplifier U1 to constitute a feedback circuit; and the output end of the second amplifier U1 is connected to an output port of the acquisition electrode module;

a reference electrode module configured to acquire an electrical signal at an earlobe based on a preset reference electrode, the reference electrode module comprising a third amplifier U3, which has an input end accessing the electrical signal acquired by the reference electrode, and an output end connected to an output port of the reference electrode module to output a first reference voltage;

a right-leg driving electrode module configured to provide a driving voltage based on a preset right-leg driving electrode, the right-leg driving electrode module comprising a fourth amplifier U4, which has an input end accessing a second reference voltage, and an output end connected to an output port of the right-leg driving electrode module; and an EEG signal output module configured to receive electrical signals output by the acquisition electrode module, the reference electrode module and the right-leg driving electrode module respectively, calculates, at each moment, a difference between voltage values of the electrical signals output by the acquisition electrode module and the reference electrode module, and a difference between voltage values of the electrical signals output by the acquisition electrode module and the right-leg driving electrode module respectively, and constructs a differential signal as an EEG signal based on the two differences.

The solution of the present disclosure is different from the prior art in which an electrical signal is output through a direct-driving electrode and then a differential signal is output. The solution of the present disclosure adds a circuit for each electrode to further process the accessed electrical signal, thereby improving the anti-interference ability of the signal. Moreover, the solution of the present disclosure provides a feedback circuit for the acquisition electrode, so as to correct the input voltage bias and further improve the anti-interference ability of the signal.

In some embodiments of the present disclosure, the first amplifier U2 with the input end connected to the output end of the second amplifier U1 is a feedback circuit amplifier, a capacitor C2 is connected between an inverted input end and an output end of the feedback circuit amplifier, an end of the capacitor C2 connected to the inverted input end of the feedback circuit amplifier is further connected to a resistor R8, and the capacitor C2 and the resistor R8 together constitute a feedback circuit of the acquisition electrode module.

In some embodiments of the present disclosure, the inverted input end of the feedback circuit amplifier is connected to a reference voltage supply end of the acquisition electrode module through the resistor R8, a non-inverted input end of the feedback circuit amplifier is connected to the reference voltage supply end of the acquisition electrode module through a resistor R7, and a resistor R3 is connected between the non-inverted input end of the feedback circuit amplifier and the output end of the second amplifier U1.

In some embodiments of the present disclosure, a fourth resistor R5 is connected between the output end of the feedback circuit amplifier and the inverted input end of the second amplifier U1.

In some embodiments of the present disclosure, a loop is further disposed between the output end and the inverted input end of the second amplifier U1, and the loop comprises a fifth resistor R4, a sixth resistor R9, a seventh resistor R6 and a second capacitor C3, wherein one end of the fifth resistor R4 is connected to the output end of the second amplifier U1, the sixth resistor R9 and the second capacitor C3 are connected in parallel, the other end of the fifth resistor R4 is connected to one common end of the sixth resistor R9 and the second capacitor C3 connected in parallel, the other common end of the sixth resistor R9 and the second capacitor C3 connected in parallel is connected to one end of the seventh resistor R6, and the other end of the seventh resistor R6 is connected to one end of the fourth resistor R5 which is connected to the inverted input end of the second amplifier U1.

In some embodiments of the present disclosure, the other common end of the sixth resistor R9 and the second capacitor C3 connected in parallel is further connected to the reference voltage supply end of the acquisition electrode module.

In some embodiments of the present disclosure, an input end of the third amplifier U3 accesses the electrical signal acquired by the reference electrode through an eighth resistor R10, and an output end of the third amplifier U3 outputs the first reference voltage through a ninth resistor R11.

In some embodiments of the present disclosure, a twelfth resistor R12 is further connected between the output end and the inverted input end of the third amplifier U3.

In some embodiments of the present disclosure, an inverted input end of the fourth amplifier U4 is connected to the second reference voltage via a tenth resistor R13, an output end of the fourth amplifier U4 is connected to an eleventh resistor R14, a third capacitor C5 is connected between the inverted input end of the fourth amplifier U4 and the output port of the right-leg driving electrode module, and one end of the third capacitor C5 is connected to one end of the eleventh resistor R14 outputting an electric signal.

In some embodiments of the present disclosure, the one end of the third capacitor C5 is connected to the one end of the eleventh resistor R14 outputting the electrical signal, and is further connected to the output port of the right-leg driving electrode module.

In some embodiments of the present disclosure, the reference electrode module further comprises a thirteenth resistor X1 with one end connected to analog ground and the other end connected to one end of a twelfth resistor R12, and the other end of the twelfth resistor R12 is connected to an inverted input end of the third amplifier U3;

the third resistor R3, the fourth resistor R5, the seventh resistor R6 and the second resistor R7 in the acquisition electrode module and the twelfth resistor R12 and the thirteenth resistor X1 in the reference electrode module satisfy the following formula:

$$X1*R7*R6=R12*(R7*R5+R3*R6+R5*R3);$$

wherein R3, R5, R6, R7, R12 and X1 represent values of the third resistor, the fourth resistor, the seventh resistor, the second resistor, the twelfth resistor and the thirteenth resistor, respectively.

In some embodiments of the present disclosure, a differential gain of the acquisition electrode module is calculated according to the following formula:

$$G=(R5/R6+1)*(R3/R7+1);$$

wherein G represents the differential gain.

Another aspect of the present disclosure provides a brain function signal acquisition method, comprising:

obtaining an EEG signal acquired by an EEG signal acquisition device and a current signal acquired by a near infrared signal acquisition device;

inputting the EEG signal acquired by the EEG signal acquisition device into a first analog-digital converter, which converts the EEG signal into a first digital signal and transmits the first digital signal to a micro-control unit for processing to obtain EEG data of a user's brain;

inputting the current signal into a transimpedance amplifier to convert the current signal into a voltage signal, and inputting the voltage signal into a second analog-to-digital converter, which converts the voltage signal into a second digital signal and transmits the second digital signal to the micro-control unit for processing to obtain functional near infrared data of the user's brain; and analyzing the EEG data and the functional near infrared data to obtain an activity situation of the user's brain.

In some embodiments, the first analog-to-digital converter and the second analog-to-digital converter respectively transmit the first digital signal and the second digital signal to the micro-control unit through an SPI protocol.

In some embodiments, the method further comprises: after the micro-control unit converts the first digital signal and the second digital signal into the EEG data and the functional near infrared data of the user's brain, transmitting the EEG data and the functional near infrared data of the user's brain to a data processing device through a Wi-Fi module, a Zigbee module and/or a Bluetooth module, so that the EEG data and the functional near infrared data of the user's brain is converted into an EEG and a functional near infrared spectrogram respectively by the data processing device.

In some embodiments, the method further comprises: before inputting the EEG signal acquired by the EEG signal acquisition device into the first analog-digital converter, sequentially performing high-pass filtering, low-pass filtering and signal amplitude amplification on the acquired EEG signal, so as to input the amplified EEG signal into the first analog-to-digital converter; wherein the high-pass filtering filters out the EEG signal with a frequency lower than 0.5 Hz, and the low-pass filtering filters out the EEG signal with a frequency higher than 200 Hz.

In some embodiments, the method further comprises: performing low-pass filtering on the voltage signal before inputting the voltage signal into the second analog-to-digital converter, so as to input the low-pass filtered voltage signal into the second analog-to-digital converter, wherein the low-pass filtering filters out the voltage signal with a frequency higher than 10 Hz.

The present disclosure has at least the following advantageous effects:

The multimodal brain function signal acquisition device and method of the present disclosure dispose the near infrared signal acquisition device and the EEG signal acquisition device on the same cap, wherein the EEG signal of the user's brain is acquired by the EEG signal acquisition device, and the current signal of the user's brain is acquired by the near infrared signal acquisition device for processing to obtain the user's EEG and functional near infrared data, which are analyzed to obtain the activity situation of the same brain part of the user at the same time. By combining the EEG and the functional near infrared data, it is helpful to understand activity situations of the user's brain more accurately.

Further, by disposing the near infrared signal acquisition device and the EEG signal acquisition device on the same cap, it is helpful to acquire the photoelectrical signals of the same brain part simultaneously, so that the detection and analysis of the same brain part are more accurate.

Further, the reflective coating on the inner wall of the light guide column can completely reflect the unabsorbed near infrared light to the photodiode, which is helpful for the photodiode to convert the unabsorbed near infrared light into current signals, and ensures the accuracy of the acquisition result of the near infrared signal acquisition device.

Additional advantages, objectives and features of the present disclosure will be partially set forth in the description below, and partially apparent to those of ordinary skill in the art upon examination of the following content, or may be learned from the practice of the present disclosure. The objectives and other advantages of the present disclosure can be realized and attained by the structure particularly pointed out in the specification and the drawings.

It will be appreciated by those skilled in the art that the objectives and advantages that can be achieved by the present disclosure are not limited to those specifically described above, and the above and other objectives that can be achieved by the present disclosure will be more clearly understood from the following detailed description.

BRIEF DESCRIPTION OF THE DRAWINGS

The drawings described here are included to provide a further understanding of the present disclosure and constitute a part of this application, rather than limiting the present disclosure. The parts in the drawings are drawn not to scale, but merely to illustrate the principle of the present disclosure. In order to facilitate the illustration and description of some parts of the present disclosure, corresponding parts in the drawings may be enlarged, i.e., they may become larger than other parts in an exemplary device actually manufactured according to the present disclosure. In the drawings.

DETAILED DESCRIPTION OF THE PREFERRED EMBODIMENTS

Figure 1:
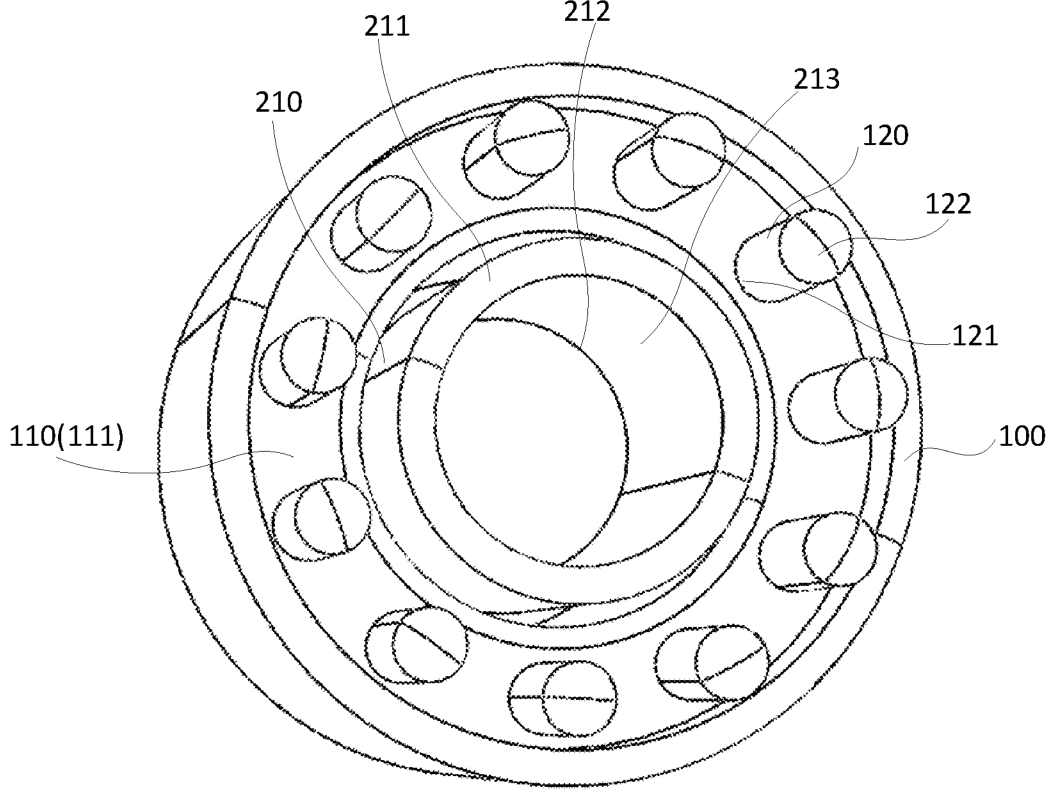
FIG. 1 is a schematic diagram of a brain signal acquisition device according to an embodiment of the present disclosure.

In order that the objectives, technical solutions and advantages of the present disclosure are clearer, the present disclosure will be further described in detail below with reference to the embodiments and the drawings. Here, the exemplary embodiments of the present disclosure and the description thereof are used to explain the present disclosure, but are not intended to limit the present disclosure.

Here, it should also be noted that, in order to avoid the present disclosure from being obscured by unnecessary details, only structures and/or processing steps closely related to the solutions according to the present disclosure are illustrated in the drawings, and other details not so related to the present disclosure are omitted.

It should be emphasized that the term 'comprise/include' used herein refers to the presence of features, elements, steps or components, but does not exclude the presence or addition of one or more other features, elements, steps or components.

Here, it should also be noted that unless otherwise specified, the term 'connection' can refer not only to a direct connection, but also to an indirect connection with an intermediate.

Hereinafter, the embodiments of the present disclosure will be described with reference to the drawings. In the drawings, the same reference numeral represents the same or similar parts, or the same or similar steps.

The brain activity can provide a variety of physiological information. Over the years, many technologies have been developed to study the brain signals from different neurophysiological mechanisms. Due to the lack of a specific technology to record the whole spectrum information generated by these signals, the multimodal synchronous monitoring method of the brain state is widely used. In the multimodal monitoring, the combination of a functional near infrared spectroscopy (FNIRS) and an electroencephalogram (EEG) has attracted more and more attention. The FNIRS is a relatively new neuroimaging technology, which has gradually become a widely used tool to monitor the brain activity because of its advantages of light weight, portability and low cost. The FNIRS is a scalp-based optical spectral measurement method, which uses a light source and a detector to measure hemodynamic changes in brain tissues. The FNIRS can record a Blood Oxygen Level-Dependent (BOLD), i.e., a compensatory hemodynamic response in a brain due to the increased oxygen demand from an activated brain area. The FNIRS depends on the differential measurement of scattered light, and is sensitive to the concentration changes of two main oscillating absorption chromophores in the near infrared spectral range, i.e., to the concentration changes of oxyhemoglobin and deoxyhemoglobin ($O_2Hb$ and HHb). $O_2Hb$ and HHb have different absorption spectra in the near infrared range (650 nm to 900 nm). Because of this characteristic and the low absorption rate of water in the same wavelength range, it is possible to measure the relative concentrations and oscillations of these substances. Over the years, the FNIRS has become a brain imaging method widely used in different populations and experimental conditions.

As the overall reflection of electrophysiological activities of brain nerve cells on the cerebral cortex or the scalp surface, also a relatively mature technology in the field of neurology and neuroimaging, the EEG captures the macro-temporal dynamics of the brain electrical activities through the passive measurement of the scalp positioning voltage. Since the EEG signals contain a large amount of physiological and disease information, the EEG system is widely used in clinical and non-clinical situations to diagnose and monitor the brain function and dysfunction. In the clinical medicine, the EEG signal processing provides not only the basis for the diagnosis of some brain diseases, but also effective treatment means for some brain diseases. In the engineering applications, people also attempt to realize a brain-computer interface (BCI) using the EEG signals, and achieve certain control purposes by effectively extracting and classifying the EEG signals according to different human EEGs for different senses, motions or cognitive activities.

The EEG activity and its corresponding hemodynamics have no perfect time-space correspondence, while their interaction is mediated by a neurovascular coupling mechanism and can be studied using combined technologies. On the contrary, when a neurovascular coupling model is assumed, a higher neural signal estimation accuracy can be obtained from the multimodal measurement. The two recording routines have many advantages: the FNIRS and the EEG technology are relatively robust against motion artifacts without significant physical limitations, especially compared with the functional magnetic resonance imaging (FMRI), the positron emission tomography (PET) or the magnetoencephalography (MEG), thereby being feasible for more natural cognitive tasks and a wide range of subjects (e.g., from infants to the elderly). In addition, the near infrared spectroscopy (NIRS) and the EEG do not involve a high-intensity magnetic field or an ionizing radiation, and the hardware costs thereof are significantly lower than those of most other functional brain imaging methods. However, in the prior art, the activity situation of the user's brain can only be monitored using the NIRS or the EEG separately rather than simultaneously. Therefore, the present disclosure provides a multimodal brain function signal acquisition device and method, so as to solve the problem that the NIRS and the NIRS cannot monitor the same brain part simultaneously and accurately in the prior art.

An aspect of the present disclosure provides a multimodal brain function signal acquisition device, as illustrated in FIG. 1, including a cap 100, an EEG signal acquisition device, a near infrared signal acquisition device, a transimpedance amplifier, a first analog-to-digital converter, a second analog-to-digital converter and a micro-control unit.

The EEG signal acquisition device includes a support member 110 and a plurality of acquisition tentacles 120. As an example, the support member is a hollow cylinder, first ends 121 of the acquisition tentacles 120 are disposed along a circumference of a first-end 111 of the support member 110, and the first end 111 is connected to the cap 100; second ends 122 of the acquisition tentacles 120 are configured to be in contact with a user's scalp and can be used as acquisition electrodes to acquire the user's EEG signal.

The near infrared signal acquisition device includes a light guide column 210, a near infrared light source and a photodiode. The light guide column is a transparent hollow cylinder with a diameter smaller than that of the support member; the light guide column is disposed within an inner periphery of the support member, the light guide column 210 has a first port 211 and a second port 212, the first port 211 is configured to be closer to the user's cerebral cortex, and the second port 212 is configured to be farther away from the user's cerebral cortex;

the near infrared light source and the photodiode are disposed at the second port 212 of the light guide column, and the first port 211 of the light guide column is fixed on the cap; near infrared light emitted by the near infrared light source arrives at the user's cerebral cortex through the light guide column; after oxyhemoglobin and deoxyhemoglobin in the user's cerebral cortex absorb the near infrared light with a specific wavelength, the unabsorbed near infrared light is scattered and arrives at the photodiode through the light guide column, and the photodiode converts the unabsorbed near infrared light into a current signal. By analyzing the current signal, the changes of oxyhemoglobin and deoxyhemoglobin in the user's brain can be obtained, thereby obtaining the motion situation of the user's brain.

Figure 11:
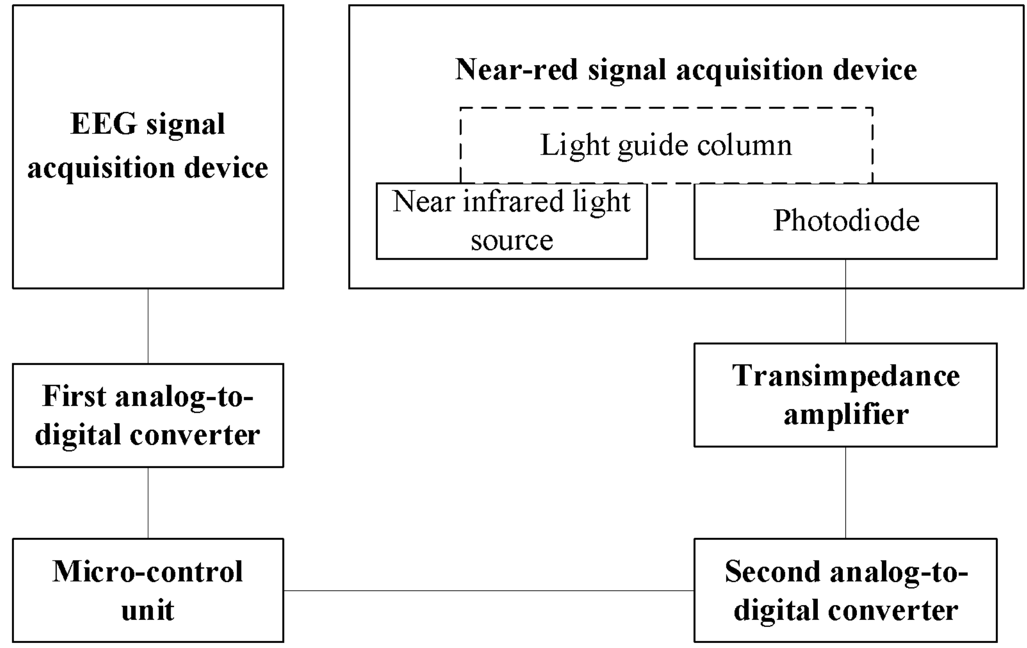
FIG. 11 is a schematic block diagram of a brain signal acquisition device according to an embodiment of the present application.

The transimpedance amplifier is connected to the photodiode and configured to convert the current signal output by the photodiode into an analog voltage signal, as illustrated in FIG. 11.

The first analog-to-digital converter is connected to the EEG signal acquisition device and configured to convert the EEG signal into a digital signal; and the second analog-to-digital converter is connected to the transimpedance amplifier and configured to convert the analog voltage signal into a digital signal.

The micro-control unit is connected to the first analog-to-digital converter and the second analog-to-digital converter, and is configured to process the first digital signal and the second digital signal after the conversions by the first analog-to-digital converter and the second analog-to-digital converter, so as to obtain EEG data and functional near infrared data respectively.

In the embodiment of the present disclosure, the multimodal brain function signal acquisition device is further mounted with a Wi-Fi module, a Zigbee module and/or a Bluetooth module to wirelessly transmit the obtained EEG data and the functional near infrared data to an external device (e.g., a host computer).

In the embodiment of the present disclosure, the cap is configured to bear the EEG signal acquisition device and the near infrared signal acquisition device and is worn on the user's head, so that the EEG signal acquisition device and the near infrared signal acquisition device can synchronously acquire signals of the same brain part. The EEG signal acquisition device and the near infrared signal acquisition device are detachably disposed on the cap, and the acquisition tentacle of the EEG signal acquisition device is fixedly disposed on the support member. The transimpedance amplifier converts the current signal into the voltage signal, so that the same signal can be transmitted to a plurality of parallel instruments. In the embodiment of the present disclosure, the near infrared light source includes red light of 740 nm and infrared light of 850 nm.

In some embodiments of the present disclosure, the multimodal brain function signal acquisition device further includes an analog circuit configured to perform high-pass filtering, low-pass filtering and signal amplitude amplification processing on the EEG signal acquired by the EEG signal acquisition device, and the processed signal is input into a first analog-digital converter; and a second-order low-pass filter circuit configured to perform low-pass filtering on the voltage signal output by the transimpedance amplifier, and the low-pass filtered voltage signal is input into a second analog-digital converter.

In some embodiments of the present disclosure, the support member and each of the acquisition tentacles may be made of a silver chloride sintered material, which has good conductivity and can better acquire bioelectrical signals from the user's cerebral cortex.

In some embodiments of the present disclosure, during acquisition of the EEG signal, each of the acquisition tentacles may be coated with conductive gel, which can quickly and effectively reduce the skin impedance and establish a stable bioelectrical signal transmission channel, so that the acquisition tentacles can more accurately acquire the bioelectrical signals from the user's cerebral cortex, thereby improving the accuracy of the acquired signals.

In some embodiment of the present disclosure, the light guide column may be made of acrylic resin, which has a low cost and a good anti-cracking performance, thereby ensuring that the light guide column of the near infrared signal acquisition device is not easy to be cracked and damaged.

In some other embodiments of the present disclosure, the light guide column may also be made of epoxy resin, glass, or polycarbonate, etc.

In some embodiment of the present disclosure, an inner wall 213 of the light guide column 210 is coated with reflective coating, which can completely reflect the near infrared light not absorbed by oxyhemoglobin and deoxyhemoglobin in the light guide column to the photodiode, thereby improving the accuracy of the acquisition result of the near infrared signal acquisition device.

Another aspect of the present disclosure provides a brain function signal acquisition method, which includes steps S101 to S104:

Step S101: obtaining an EEG signal acquired by an EEG signal acquisition device and a current signal acquired by a near infrared signal acquisition device.

Step S102: inputting the EEG signal acquired by the EEG signal acquisition device to a first analog-digital converter, which converts the EEG signal into a first digital signal and transmits the first digital signal to a micro-control unit for processing to obtain EEG data of a user's brain.

Step S103: inputting the current signal into a transimpedance amplifier to convert the current signal into an analog voltage signal, and inputting the analog voltage signal into a second analog-to-digital converter, which converts the analog voltage signal into a second digital signal and transmits the second digital signal to the micro-control unit for processing to obtain functional near infrared data of the user's brain.

Step S104: analyzing the EEG data and the functional near infrared data to obtain an activity situation of the user's brain.

In step S101, the multimodal brain function signal acquisition device including the EEG signal acquisition device and the near infrared signal acquisition device of the present disclosure is worn on the user's head, wherein an acquisition tentacle of the EEG signal acquisition device contacts the user's scalp to acquire the user's EEG signal; a near infrared light source of the near infrared signal acquisition device reflects near infrared light to arrive at the user's cerebral cortex through a light guide column; after oxyhemoglobin and deoxyhemoglobin in the user's cerebral cortex absorb the near infrared light with a specific wavelength, the unabsorbed near infrared light is scattered and arrives at a photodiode through the light guide column, and the photodiode converts the unabsorbed near infrared light into a current signal.

In some embodiments of the present disclosure, the method further includes: before inputting the EEG signal acquired by the EEG signal acquisition device into the first analog-to-digital converter, sequentially performing high-pass filtering, low-pass filtering and signal amplitude amplification on the acquired EEG signal, so as to input the amplified EEG signal into the first analog-to-digital converter.

Figure 2:
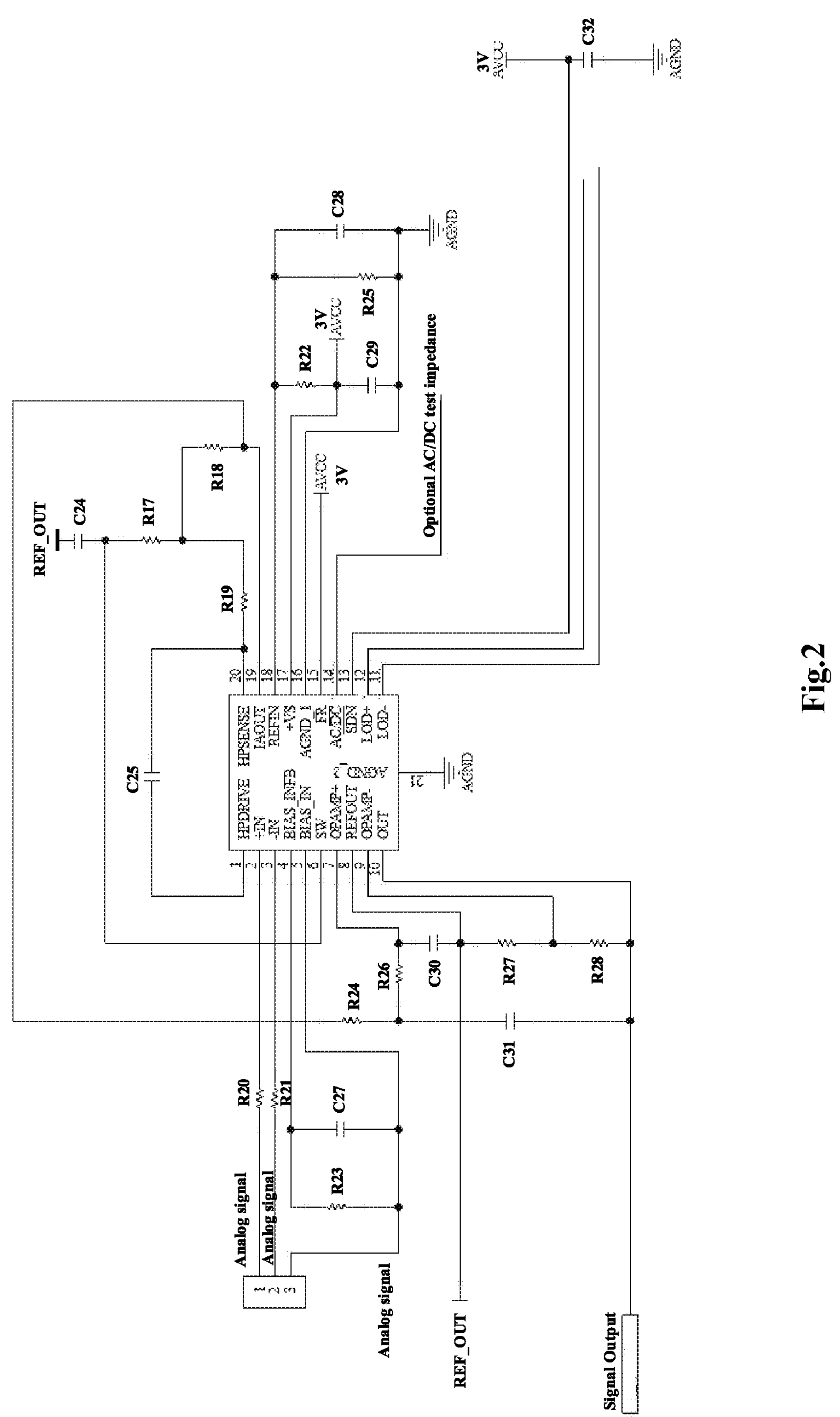
FIG. 2 is a schematic diagram of an analog circuit according to an embodiment of the present disclosure.

As an example, in step S102, as illustrated in FIG. 2, the EEG signal is input into an analog circuit, which includes a high-pass filter circuit, a low-pass filter circuit and an amplifier circuit. Firstly, the analog circuit performs high-pass filtering on the EEG signal via the high-pass filter circuit to filter out the EEG signal with a frequency lower than 0.5 Hz, and the high-pass filtering can filter out the interference noise. Next, the analog circuit performs low-pass filtering on the high-pass filtered EEG signal via the low-pass filter circuit to filter out the EEG signal with a frequency higher than 200 Hz, and the low-pass filtering can filter out some high-frequency signals such as electromyographic (EMG) signals, which is helpful to improve the accuracy of the EEG signal analysis. Further, the power of the low-pass filtered EEG signal is amplified by the amplifier circuit, which is helpful to amplify the acquired weak EEG signal, so that the obtained EEG is more accurate.

Figure 3:
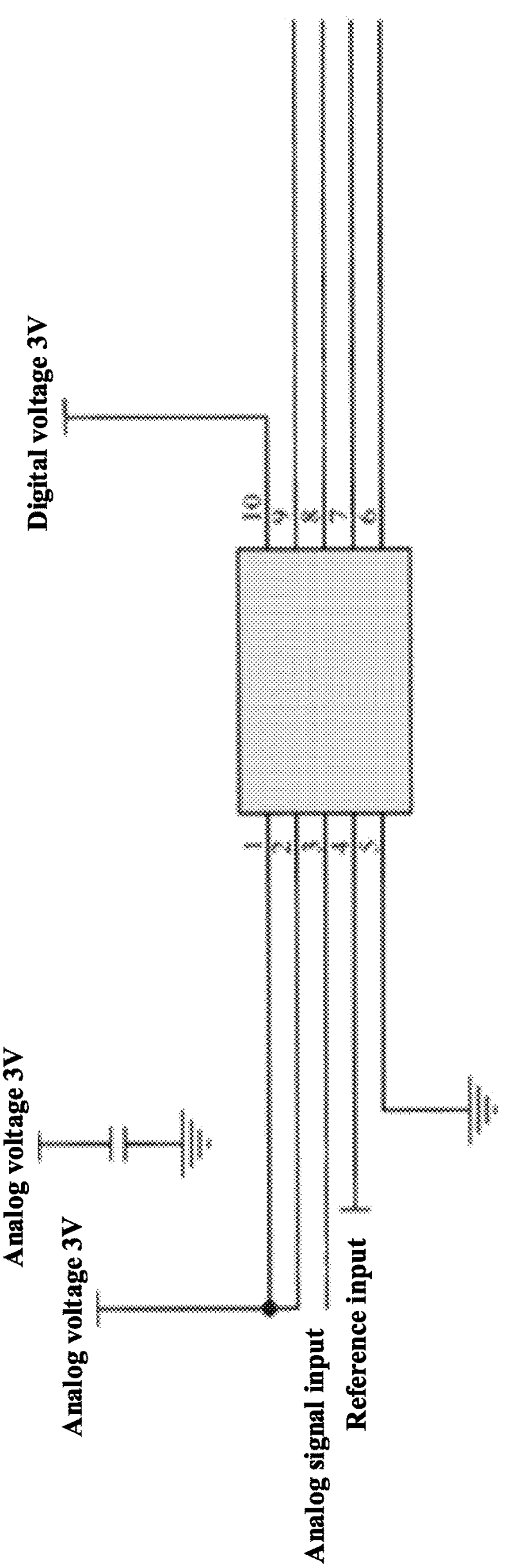
FIG. 3 is a schematic diagram of an internal circuit structure of a first analog-to-digital converter according to an embodiment of the present disclosure.

As illustrated in FIG. 3, the first analog-to-digital converter converts the EEG signal with the amplified signal amplitude into a first digital signal, wherein the first analog-to-digital converter may adopt a model of AD7989-1BRMZ, but the present disclosure is not limited thereto. The first analog-to-digital converter transmits the first digital signal to the micro-control unit through an SPI protocol to further obtain the user's EEG data, and the micro-control unit transmits the user's EEG data to a data processing device through a Bluetooth module for processing to obtain the EEG of the user's brain.

In some embodiments, the method further includes: performing low-pass filtering on the voltage signal before inputting the voltage signal into the second analog-to-digital converter. The low-pass filtered voltage signal is input into the second analog-to-digital converter.

Figure 4:
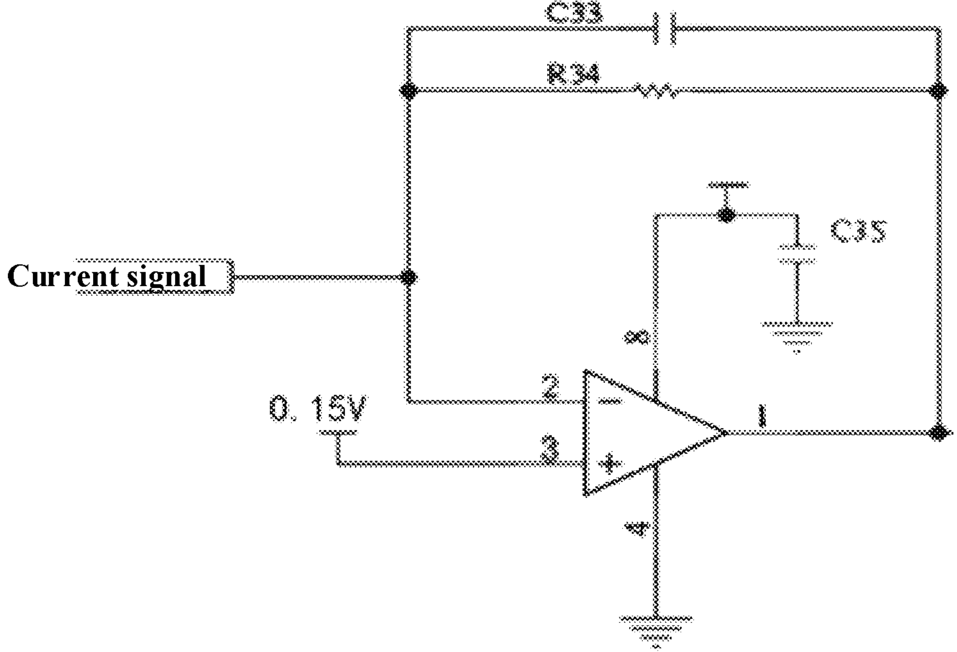
FIG. 4 is a schematic diagram of a transimpedance amplifier circuit according to an embodiment of the present disclosure.
Figure 5:
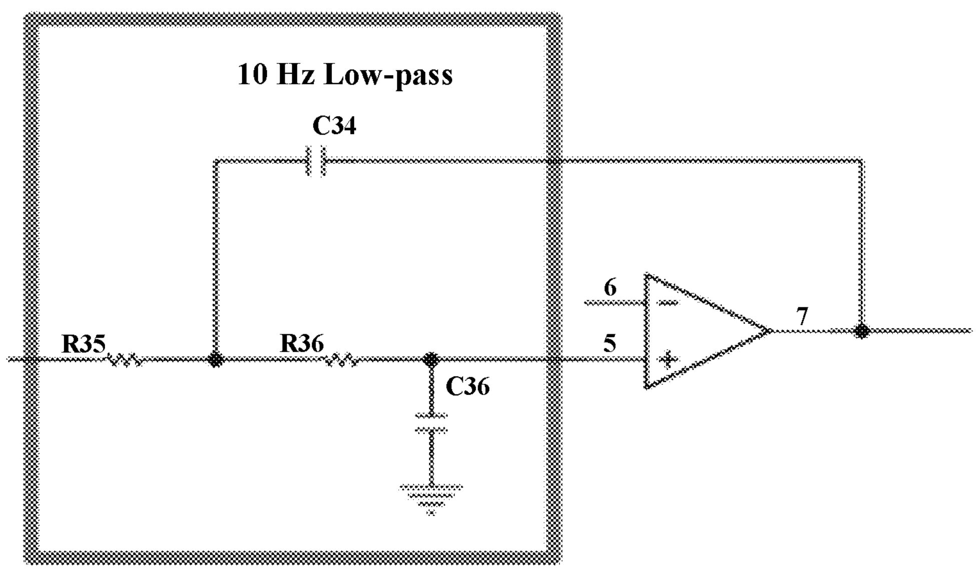
FIG. 5 is a schematic diagram of a second-order low-pass filter circuit according to an embodiment of the present disclosure.
Figure 6:
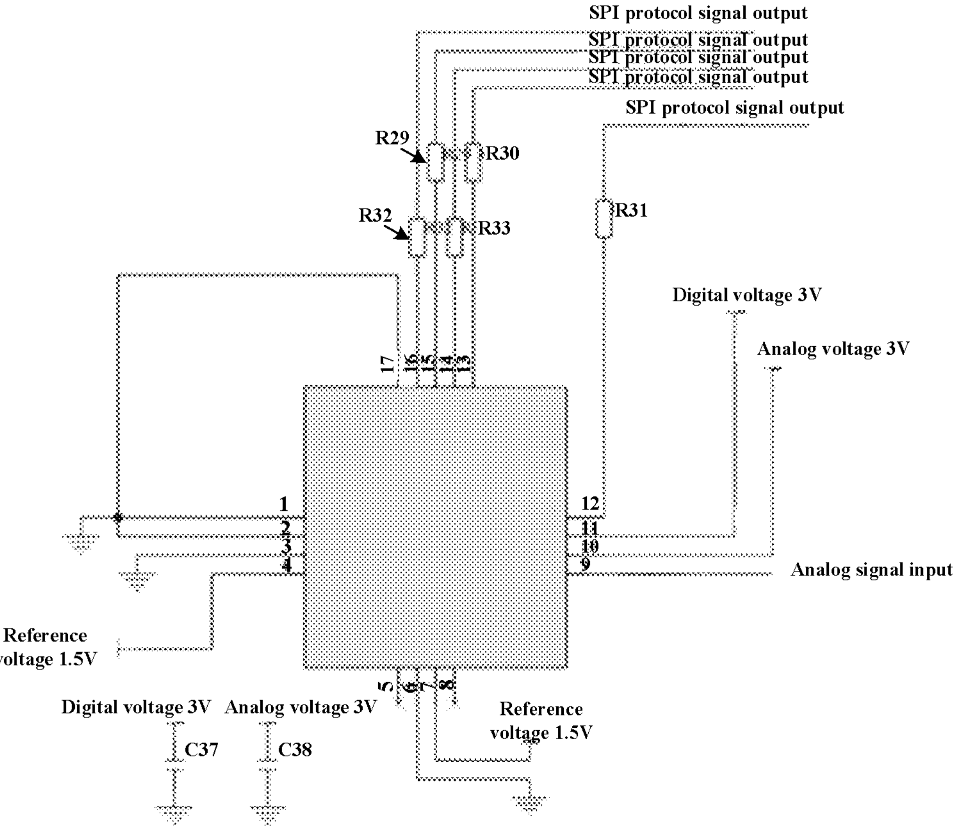
FIG. 6 is a schematic diagram of an internal circuit structure of a second analog-to-digital converter according to an embodiment of the present disclosure.

As an example, in step S103, as illustrated in FIG. 4, the current signal acquired by the near infrared signal acquisition device is converted into a voltage signal by a transimpedance amplifier. As illustrated in FIG. 5, the voltage signal is input into a second-order low-pass filter circuit for low-pass filtering to filter out the voltage signal with a frequency higher than 10 Hz. The low-pass filtered voltage signal is converted into a second digital signal by a second analog-to-digital converter as illustrated in FIG. 6, wherein the second analog-to-digital converter may adopt a model of ADS1120, but the present disclosure is not limited thereto. The second analog-to-digital converter transmits the second digital signal to a micro-control unit through an SPI protocol to obtain functional near infrared data of the user's brain, and the micro-control unit transmits the functional near infrared data of the user's brain to a data processing device through a Bluetooth module for processing to obtain a functional near infrared spectrogram of the user's brain.

In some embodiments, after the micro-control unit converts the first digital signal and the second digital signal into the EEG data and the functional near infrared data of the user's brain, the data of the user's brain may be transmitted to a host computer through a Wi-Fi module, a Zigbee module and/or a Bluetooth module, and the host computer processes the data of the user's brain and obtains the EEG and the functional near infrared data of the user's brain. The convenience of data transmission is improved by means of wireless connection.

In step S104, the user's EEG and functional near infrared spectrogram are combined and analyzed to obtain the activity situation of the user's brain, thereby improving the accuracy of monitoring of the user's brain through the multimodal monitoring technology.

To sum up, the multimodal brain function signal acquisition device and method of the present disclosure dispose the near infrared signal acquisition device and the EEG signal acquisition device on the same cap, wherein the EEG signal of the user's brain is acquired by the EEG signal acquisition device, and the current signal of the user's brain is acquired by the near infrared signal acquisition device for processing to obtain the user's EEG and functional near infrared data, which are analyzed to obtain the activity situation of the same brain part of the user at the same time. By combining the EEG and the functional near infrared data, it is helpful to understand activity situations of the user's brain more accurately.

Further, by disposing the near infrared signal acquisition device and the EEG signal acquisition device on the same cap, it is helpful to acquire the photoelectrical signals of the same brain part simultaneously, so that the detection and analysis of the same brain part are more accurate.

Further, the reflective coating on the inner wall 213 of the light guide column 210 can completely reflect the unabsorbed near infrared light to the photodiode, which is helpful for the photodiode to convert the unabsorbed near infrared light into current signals, and ensures the accuracy of the acquisition result of the near infrared signal acquisition device.

In some embodiments of the present disclosure, the circuit of the EEG signal acquisition device may be that of the existing EEG signal acquisition device. Although the acquisition of the EEG signal is a relatively mature technology in the field of neurology and neuroimaging, the acquisition and processing of the EEG signal has always been a very attractive but difficult research topic because the EEG signal is a non-stationary random signal without ergodicity and with strong background noise.

In the prior art, an electrical signal is usually acquired by a direct-driving electrode, and then a differential signal is output as an EEG signal. However, the electrode adopted to acquire the EEG signal is the direct-driving electrode, and there is no intervention of an active signal or measures such as a processing circuit, so the signal interference is serious since the acquired EEG signal is at a millivolt level.

Figure 7:
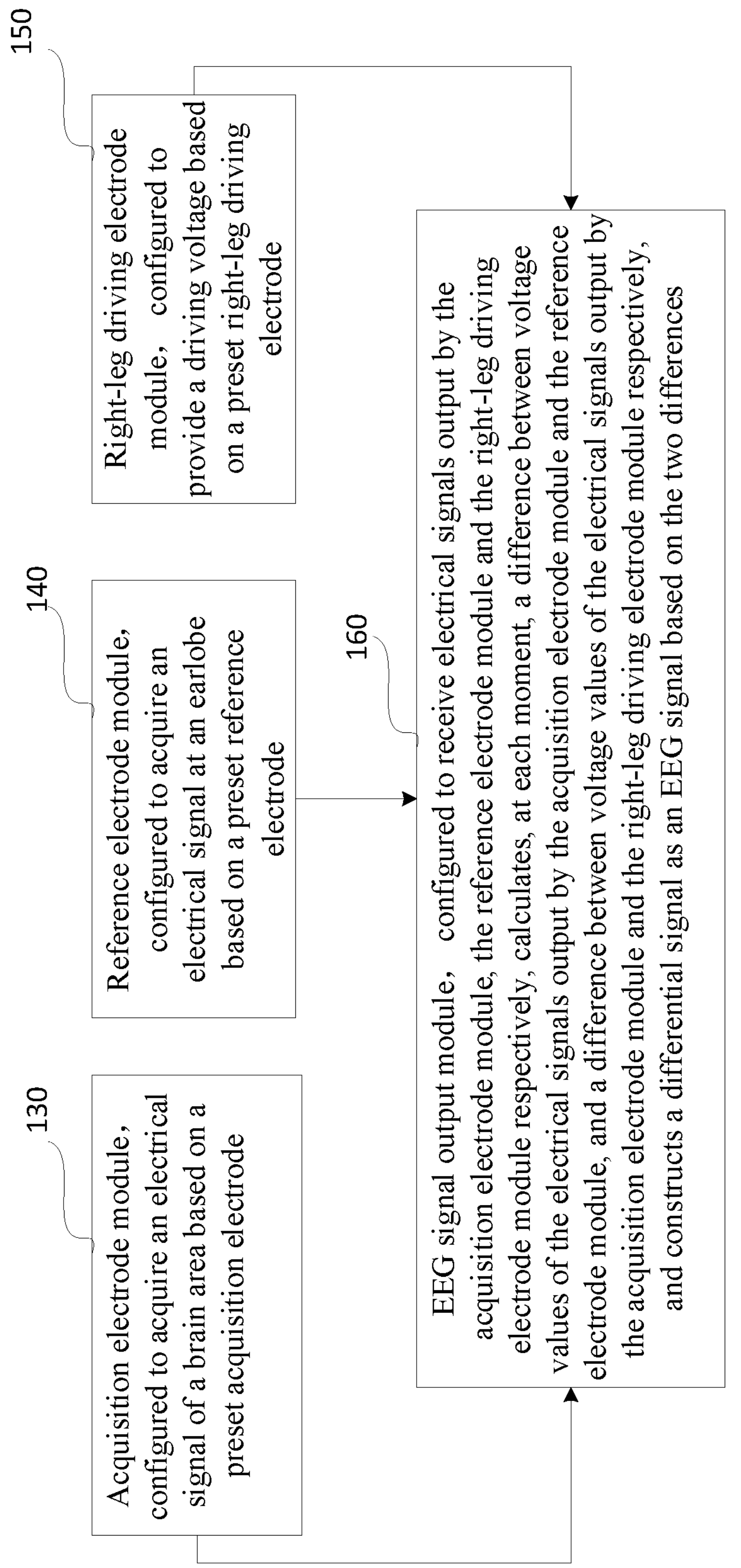
FIG. 7 is a schematic diagram of a structure of an improved electroencephalogram (EEG) signal acquisition device according to an embodiment of the present disclosure.

In this regard, the present disclosure further provides an improved EEG signal acquisition device. As illustrated in FIG. 7, in addition to the support member 110 and the plurality of acquisition tentacles 120, the improved EEG signal acquisition device further includes an acquisition electrode module 130, a reference electrode module 140, a right-leg driving electrode module 150 and an EEG signal output module 160.

Figure 8:
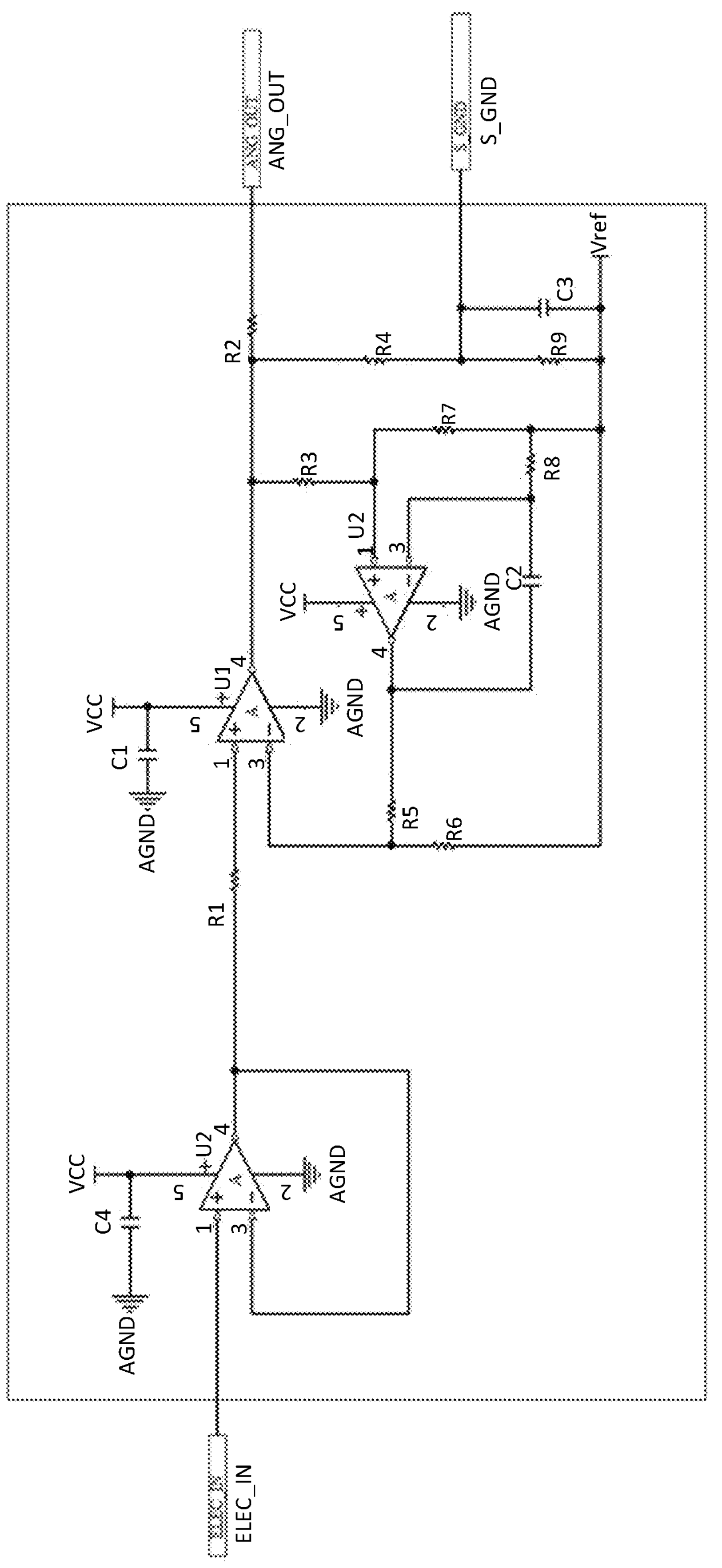
FIG. 8 is a schematic diagram of a circuit structure of an acquisition electrode module according to an embodiment of the present disclosure.

As illustrated in FIG. 8, the acquisition electrode module 130 is configured to acquire an electrical signal of a brain area based on a preset acquisition electrode, and includes two first amplifiers U2 and a second amplifier U1, wherein an input end of one of the first amplifiers U2 is configured to access the electrical signal acquired by the acquisition electrode, and an input end of the second amplifier U1 is connected to an output end of the first amplifier U2 accessing the acquired electrical signal; an input end of the other of the first amplifiers U2 is connected to an output end of the second amplifier U1, and an output end of the other of the first amplifiers U2 is connected to the input end of the second amplifier U1 to constitute a feedback circuit; and the output end of the second amplifier U1 is connected to an output port of the acquisition electrode module.

In a specific embodiment, the first amplifier U2 having its input end accessing the electrical signal acquired by the acquisition electrode is a follower amplifier, which doubles the accessed signal to improve the impedance and isolate the interference.

In FIG. 8, ELEC_IN represents an input end of the acquisition electrode module, ANG_OUT represents an output end of the acquisition electrode module, S_GND represents a signal ground, VCC represents a power supply voltage, AGND represents an analog ground and Vref represents a third reference voltage.

In some embodiments of the present disclosure, the other of the first amplifiers U2 has the input end connected to the output end of the second amplifier U1, and the output end connected to the input end of the second amplifier U1, so as to constitute a feedback circuit which is integrated to correct an input voltage bias.

In the prior art, there is an interference on the unprocessed signal acquired by the electrode, because the EEG signal is weak, mainly at the mv level; if the test environment is in a strong electromagnetic environment, electromagnetic waves can easily interfere with the weak signal and drown it in noise; the EMG noise generated by exercise and the power frequency will also affect the signal. The solution improves the circuit from the source of the circuit design. Since the EEG signal is at the microvolt level and can be easily interfered by the environment, the signal is processed at the signal source in the present disclosure, and then the processed signal is transmitted to better shield the interference.

Figure 9:
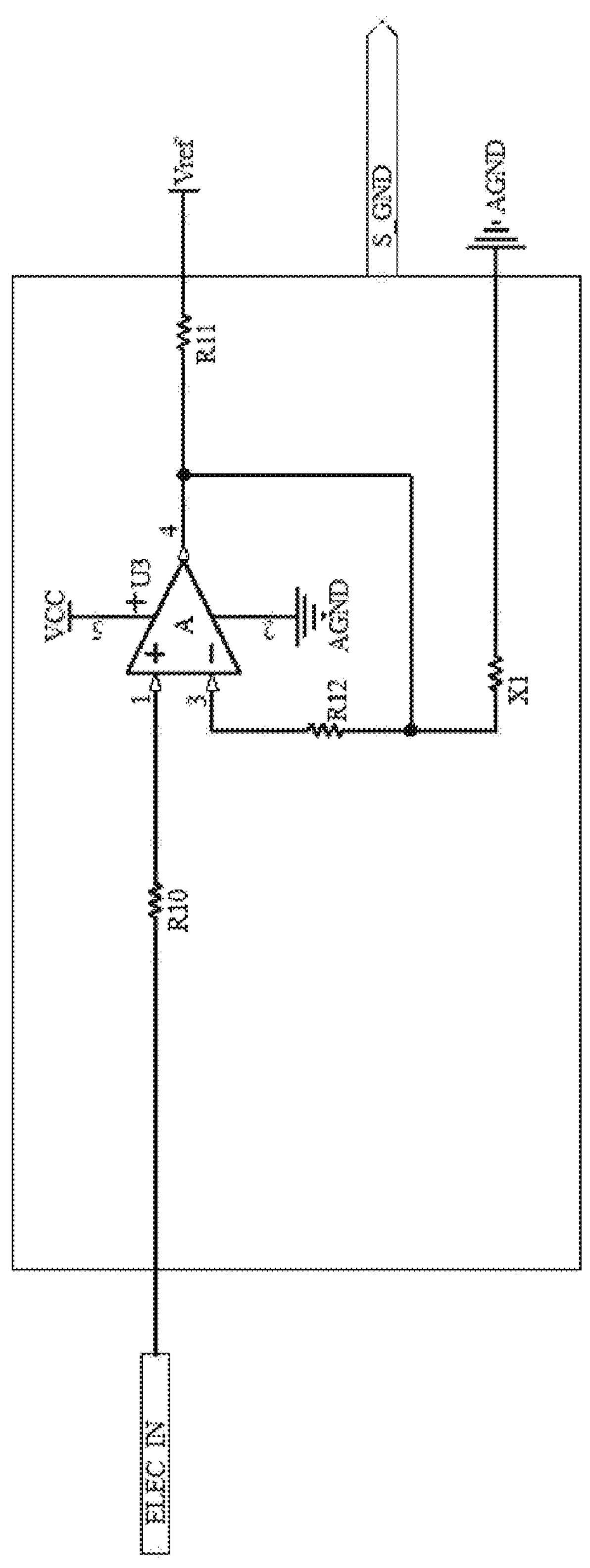
FIG. 9 is a schematic diagram of a circuit structure of a reference electrode module according to an embodiment of the present disclosure.

As illustrated in FIG. 9, the reference electrode module 140 is configured to acquire an electrical signal at an earlobe based on a preset reference electrode, and includes a third amplifier U3, which has an input end accessing the electrical signal acquired by the reference electrode, and an output end connected to an output port of the reference electrode module to output a first reference voltage.

In FIG. 9, ELEC_IN represents an input end of the reference electrode module, Vref represents an output port of the reference electrode module, S_GND represents a signal ground, VCC represents a power supply voltage, AGND represents an analog ground, and Vref represents a first reference voltage.

Figure 10:
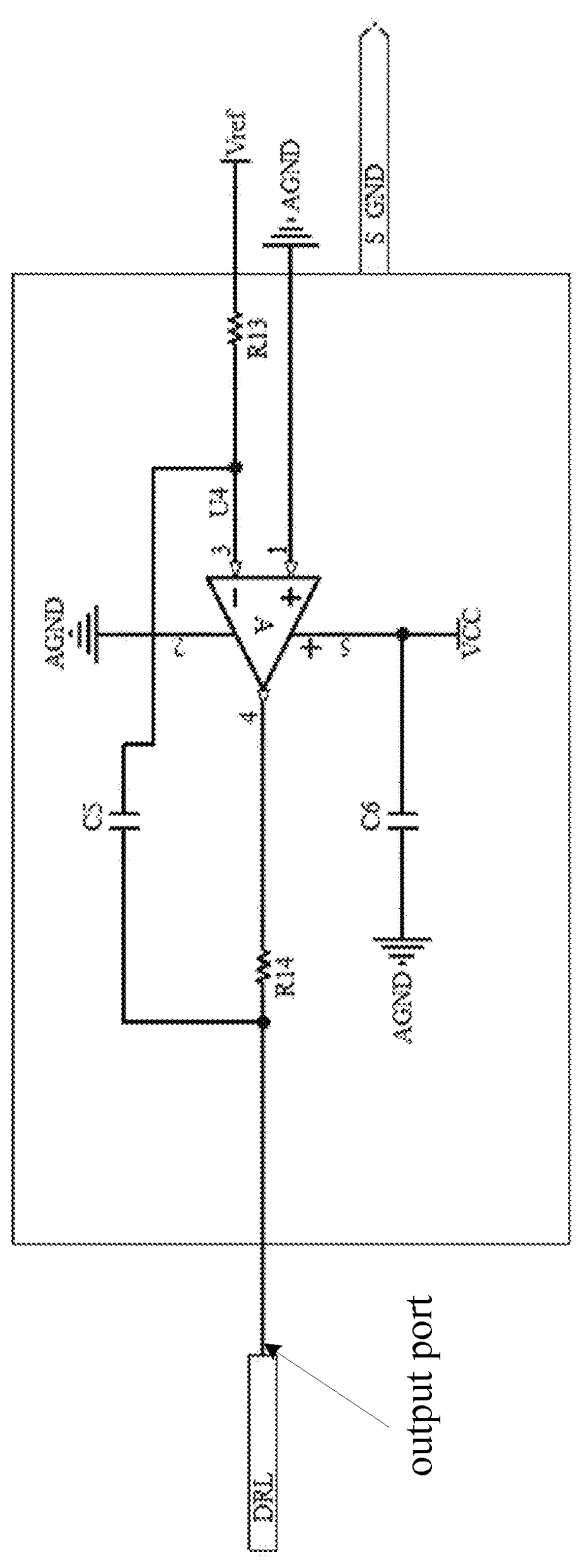
FIG. 10 is a schematic diagram of a circuit structure of a right-leg driving electrode module according to an embodiment of the present disclosure.

As illustrated in FIG. 10, a right-leg driving electrode module 150 is configured to provide a driving voltage based on a preset right-leg driving electrode, and includes a fourth amplifier U4, which has an input end accessing a second reference voltage, and an output end connected to an output port of the right-leg driving electrode module.

In FIG. 10, DRL represents an electrical signal output by the right-leg driving electrode module, i.e., a driving signal generated by the driving electrode. In FIG. 10, S GND represents a signal ground, VCC represents a power supply voltage, AGND represents an analog ground, and Vref represents a second reference voltage.

In a specific embodiment, the right-leg driving electrode module is configured to suppress a common-mode interference.

In a specific embodiment, the first reference voltage, the second reference voltage and the third reference voltage may be the same voltage parameter value.

The EEG signal output module 160 receives electrical signals output by the acquisition electrode module, the reference electrode module and the right-leg driving electrode module respectively, calculates, at each moment, a difference between voltage values of the electrical signals output by the acquisition electrode module and the reference electrode module, and a difference between voltage values of the electrical signals output by the acquisition electrode module and the right-leg driving electrode module respectively, and constructs a differential signal as an EEG signal based on the two differences.

This solution adopted by the present disclosure is different from the prior art in which an electrical signal is output through a direct-driving electrode and then a differential signal is output. This solution adds a circuit for each electrode to further process the accessed electrical signal, thereby improving the anti-interference ability of the signal. Moreover, this solution provides a feedback circuit for the acquisition electrode, so as to correct the input voltage bias and further improve the anti-interference ability of the signal.

In some embodiments of the present disclosure, as illustrated in FIG. 8, the first amplifier U2 with the input end connected to the output end of the second amplifier U1 is a feedback circuit amplifier, a capacitor C2 is connected between an inverted input end and an output end of the feedback circuit amplifier, an end of the capacitor C2 connected to the inverted input end of the feedback circuit amplifier is further connected to a resistor R8, and the capacitor C2 and the resistor R8 together constitute a feedback circuit of the acquisition electrode module.

In the above solution of the present disclosure, the feedback circuit is composed of the feedback circuit amplifier, the capacitor C2, the resistor R8, etc., so that the input voltage bias can be corrected, thereby further improving the anti-interference ability of the signal.

In some embodiments of the present disclosure, the inverted input end of the feedback circuit amplifier is connected to a reference voltage supply end of the acquisition electrode module through the resistor R8, a non-inverted input end of the feedback circuit amplifier is connected to the reference voltage supply end of the acquisition electrode module through a resistor R7, and a resistor R3 is connected between the non-inverted input end of the feedback circuit amplifier and the output end of the second amplifier U1.

In some embodiments of the present disclosure, a resistor R5 is connected between the output end of the feedback circuit amplifier and an inverted input end of the second amplifier U1.

In some embodiments of the present disclosure, a loop is further disposed between the output end and the inverted input end of the second amplifier U1. The loop includes a resistor R4, a resistor R9, a resistor R6 and a capacitor C3, wherein one end of the resistor R4 is connected to the output end of the second amplifier U1, the resistor R9 and the capacitor C3 are connected in parallel, the other end of the resistor R4 is connected to one common end of the resistor R9 and the capacitor C3 connected in parallel, the other common end of the resistor R9 and the capacitor C3 connected in parallel is connected to one end of the resistor R6, and the other end of the resistor R6 is connected to the inverted input end of the second amplifier U1.

In some embodiments of the present disclosure, the other common end of the resistor R9 and the capacitor C3 connected in parallel is further connected to the reference voltage supply end of the acquisition electrode module, so as to be provided with the third reference voltage.

As illustrated in FIG. 8, in a specific embodiment, a fifth pin of the first amplifier U2, which has the input end accessing the electrical signal acquired by the acquisition electrode, is supplied with a power supply voltage, and a capacitor C4 is connected in a connecting line with the analog ground; a second pin of the second amplifier U2, which has the input end accessing the electrical signal acquired by the acquisition electrode, is connected to the analog ground; a resistor R1 is connected between the output end of the second amplifier U2, which has the input end accessing the electrical signal acquired by the acquisition electrode, and the non-inverted input end of the second amplifier U1; the fifth pin of the second amplifier U1 is supplied with the power supply voltage, and a capacitor C1 is connected in the connecting line with the analog ground; the second pin of the second amplifier U1 is connected to the analog ground; a resistor R2 is provided between the output end of the second amplifier U1 and an output port ANG_OUT of the acquisition electrode module; the second pin of the feedback circuit amplifier U2 is connected to analog ground, and the fifth pin is supplied with the power supply voltage.

As illustrated in FIG. 9, in some embodiments of the present disclosure, a non-inverted input end of the amplifier U3 of the reference electrode module accesses the electrical signal acquired by the reference electrode through the resistor R10, and an output end of the amplifier U3 outputs the first reference voltage through the resistor R11.

In some embodiments of the present disclosure, a resistor R12 is further connected between the output end and the inverted input end of the amplifier U3.

As illustrated in FIG. 9, in a specific embodiment, the second pin of the amplifier U3 is connected to the analog ground, and the fifth pin is supplied with the power supply voltage.

In a specific embodiment, the reference electrode module is configured to provide a reference calculation standard voltage, i.e., the first reference voltage, for signal calculation.

As illustrated in FIG. 10, in some embodiments of the present disclosure, an inverted input end of the amplifier U4 of the right-leg driving electrode module is connected to the second reference voltage through a resistor R13, and an output end of the amplifier U4 is connected to a resistor R14, and a capacitor C5 is further connected between the inverted input end of the amplifier U4 and the output port of the right-leg driving electrode module. More specifically, a capacitor C5 is connected between the inverted input end of the amplifier U4 and one end of the resistor R14 which outputs an electrical signal DRL. That is, the capacitor C5 has one end connected to the inverted input end of the amplifier U4, and the other end connected to the output port of the right-leg driving electrode module.

As illustrated in FIG. 10, in a specific embodiment, a fifth pin of the amplifier U4 is supplied with a power supply voltage, and a capacitor C6 is connected in the connecting line with the analog ground; a second pin of amplifier U4 is connected to the analog ground; a first pin of the non-inverted input end of the amplifier U4 is connected to the analog ground.

In some embodiments of the present disclosure, the reference electrode module further includes a resistor X1, which has one end connected to the analog ground, and the other end connected to one end of the resistor R12, and the other end of the resistor R12 is connected to the inverted input end of the amplifier U3.

The resistors R3, R5, R6 and R7 in the acquisition electrode module and the resistors R12 and X1 in the reference electrode module satisfy the following formula:

$$X1*R7*R6=R12*(R7*R5+R3*R6+R5*R3).$$

In some embodiments of the present disclosure, a differential gain of the acquisition electrode module is calculated according to the following formula:

$$G=(R5/R6+1)*(R3/R7+1);$$

where G represents the differential gain.

In a specific embodiment, a common mode rejection ratio of this solution is calculated according to the following formula:

$$CMRR=20*lg(50*G/\text{total error});$$

where CMRR represents a common mode rejection ratio parameter, G represents the differential gain, and the total error is a sum of error parameters of all of the capacitors and the resistors in the EEG signal acquisition device.

The error parameters of the capacitors and the resistors are calibrated in advance by the manufacturers.

In a specific embodiment, the acquisition electrode module, the reference electrode module and the right-leg driving electrode module in this solution have similar physical structures, which may include a probe, a circuit, a shielding cover and a shielding wire. The probe is connected to the circuit to input the acquired electrical signal thereto, the probe may be made of copper and silver plating, the probe is connected to the circuit through a base which may be made of cooper-plating silver or nickel-plating brass, and the base and the probe may be prepared by a computer numerical control (CNC) process to ensure the integration. The circuit structure is disposed on a circuit board, which may be connected to the base of the probe by welding. The shielding cover is a metal shell wrapping the parts above the electrode. The shielding wire is a shielding layer woven into a grid-shape with a characteristic impedance of 50 ohms.

In a specific embodiment, the structure of the electrode is a probe, i.e., a needle-type electrode. The electrode and the signal acquisition board are made together, the signal input is isolated by a designed follower circuit, and then it turns to a next stage of amplification circuit for processing. The reference electrode module circuit and the acquisition electrode module circuit acquire and process signals, and the right-leg driving electrode substantially filter out the common-mode signal. A higher common mode rejection ratio can be obtained through the gain of the amplifier circuit and by controlling the tolerances of components.

The signal is output to the data processing end of the amplifier by ANG_OUT of the acquisition electrode module.

By adopting the above solution, the acquisition electrode, the reference electrode and the right-leg driving electrode in this solution all have power supplies and signal processing circuits, so that the common-mode noise can be suppressed and the input impedance can be increased. A total impedance balance formula is put forward, so that the calculated common-mode gain is close to zero.

Another aspect of the present disclosure provides an improved EEG signal acquisition device, which includes an acquisition electrode module, a reference electrode module, a right-leg driving electrode module and an EEG signal output device.

The acquisition electrode module is configured to acquire an electrical signal of a brain area based on a preset acquisition electrode, and includes two first amplifiers U2 and a second amplifier U1, wherein an input end of one of the first amplifiers U2 is configured to access the electrical signal acquired by the acquisition electrode, and an input end of the second amplifier U1 is connected to an output end of the first amplifier U2 accessing the acquired electrical signal; an input end of the other of the first amplifiers U2 is connected to an output end of the second amplifier U1, and an output end of the other of the first amplifiers U2 is connected to the input end of the second amplifier U1 to constitute a feedback circuit; and the output end of the second amplifier U1 is connected to an output port of the acquisition electrode module.

The reference electrode module is configured to acquire an electrical signal at an earlobe based on a preset reference electrode, and includes a third amplifier U3, which has an input end accessing the electrical signal acquired by the reference electrode, and an output end connected to an output port of the reference electrode module to output a first reference voltage.

The right-leg driving electrode module is configured to provide a driving voltage based on a preset right-leg driving electrode, and includes a fourth amplifier U4, which has an input end connected to a second reference voltage, and an output end connected to an output port of the right-leg driving electrode module.

The EEG signal output device receives the electrical signals output by the acquisition electrode, the reference electrode and the right-leg driving electrode respectively, calculates, at each moment, a difference between voltage values of the electrical signals output by the acquisition electrode and the reference electrode, and a difference between voltage values of the electrical signals output by the acquisition electrode and the right-leg driving electrode respectively, and constructs a differential signal as an EEG signal based on the two differences.

The improved EEG signal acquisition device of the present disclosure adds a circuit for each electrode to further process the accessed electrical signal, thereby improving the anti-interference ability of the signal. Moreover, the improved EEG signal acquisition device of the present disclosure may be provided with a feedback circuit, so as to correct the input voltage bias and further improve the anti-interference ability of the signal.

The improved EEG signal acquisition device of the present disclosure may also be used independently from the multimodal brain function signal acquisition device.

Those of ordinary skill in the art will appreciate that the various exemplary components, systems, and methods described in conjunction with the embodiments disclosed herein can be implemented by hardware, software, or a combination thereof. The implementation mode depends on the specific application and design constraints of the technical solutions. Skilled persons can implement the described functions for each particular application using different methods, but such implementations should not be construed as going beyond the scope of the present disclosure. When the implementation is made by hardware, the hardware may be, for example, an electronic circuit, an application specific integrated circuit (ASIC), appropriate firmware, a plug-in, a function card, etc. When the implementation is made by software, the elements of the present disclosure are programs or code segments that are used to perform required tasks. A program or code segment may be stored in a machine-readable medium, or transmitted in a transmission medium or a communication link by a data signal carried in a carrier wave.

It should be noted that the present disclosure is not limited to the specific configurations and processes described above and illustrated in the drawings. The detailed descriptions of known methods are omitted here for the sake of brevity. In the above embodiments, several specific steps are described and illustrated as examples. However, the method process of the present disclosure is not limited to the specific steps described and illustrated, and various variations, modifications, additions, or changes in the order of the steps can be made by those skilled in the art after grasping the spirit of the present disclosure.

In the present disclosure, features described and/or illustrated for one embodiment can be used in the same way or in a similar way in one or more other embodiments, and/or combined with or substituted for features of other embodiments.

Those described above are merely preferred embodiments of the present disclosure, rather than limitations thereto. Various modifications and variations of the embodiments of the present disclosure will be apparent to those skilled in the art. Any modification, equivalent substitution, improvement, etc. made within the spirit and principle of the present disclosure should be included in the protection scope of the present disclosure.

The invention claimed is:

1. A multimodal brain function signal acquisition device, comprising:

- a cap configured to bear an electroencephalogram (EEG) signal acquisition device and a near infrared signal acquisition device;
- the (EEG) signal acquisition device which comprises a support member and a plurality of acquisition tentacles as acquisition electrodes; the support member is a hollow cylinder, a first end of the support member is connected to the cap, a first ends of the acquisition tentacles are disposed along a circumference of the first end of the support member; a second ends of the acquisition tentacles are configured to be in contact with a user's scalp to acquire the user's EEG signal;
- a near-red signal acquisition device which comprises a light guide column, a near infrared light source and a photodiode; wherein the light guide column is a transparent hollow cylinder with a diameter smaller than that of the support member; the light guide column is fixed on the cap and is disposed within an inner periphery of the support member, the light guide column has a first port and a second port, the first port of the light guide column is configured to be closer to the user's cerebral cortex, and the second port of the light guide column is configured to be farther away from the user's cerebral cortex; the near infrared light source and the photodiode are disposed at the second port of the light guide column; after near infrared light emitted by the near infrared light source arrives at the user's cerebral cortex through the light guide column; the photodiode receives near infrared light not absorbed by oxyhemoglobin and deoxyhemoglobin of the user's cerebral cortex which is scattered and arrives at the photodiode through the light guide column, and converts the unabsorbed near infrared light into a current signal;
- a transimpedance amplifier connected to the photodiode and configured to convert the current signal into an analog voltage signal;
- a first analog-to-digital converter connected to the EEG signal acquisition device and configured to convert the EEG signal into a first digital signal;
- a second analog-to-digital converter connected to the transimpedance amplifier and configured to convert the analog voltage signal into a second digital signal; and
- a micro-control unit connected to the first analog-to-digital converter and the second analog-to-digital converter, and configured to receive the first digital signal output by the first analog-to-digital converter and the second digital signal output by the second analog-to-digital converter.

2. The multimodal brain function signal acquisition device according to claim 1, wherein the support member and each of the acquisition tentacles are made of silver chloride, and the light guide column is made of acrylic resin, epoxy resin, glass or polycarbonate.

3. The multimodal brain function signal acquisition device according to claim 2, wherein during the acquisition of the EEG signal, each of the acquisition tentacles is coated with conductive gel.

4. The multimodal brain function signal acquisition device according to claim 1, further comprising an analog circuit configured to perform high-pass filtering, low-pass filtering and signal amplitude amplification processing on the EEG signal acquired by the EEG signal acquisition device, and the processed signal is input into the first analog-digital converter; and a second-order low-pass filter circuit configured to perform low-pass filtering on the analog voltage signal converted by the transimpedance amplifier, and the low-pass filtered voltage signal is input into the second analog-digital converter.

5. The multimodal brain function signal acquisition device according to claim 1, wherein an inner wall of the light guide column is coated with reflective coating.

6. The multimodal brain function signal acquisition device according to claim 1, wherein the EEG signal acquisition device further comprises:

an acquisition electrode module configured to acquire an electrical signal of a brain area based on the plurality of acquisition tentacles as acquisition electrodes, the acquisition electrode module comprising two first amplifiers (U2) and a second amplifier (U1), wherein an input end of one of the first amplifiers (U2) is configured to access the electrical signal acquired by the acquisition electrode, and an input end of the second amplifier (U1) is connected to an output end of the first amplifier (U2) accessing the acquired electrical signal; an input end of the other of the first amplifiers (U2) is connected to an output end of the second amplifier (U1), and an output end of the other of the first amplifiers (U2) is connected to the input end of the second amplifier (U1) to constitute a feedback circuit; and the output end of the second amplifier (U1) is connected to an output port of the acquisition electrode module;

a reference electrode module configured to acquire an electrical signal at an earlobe based on a preset reference electrode of the reference electrode module, the reference electrode module comprising a third amplifier (U3), which has an input end accessing the electrical signal acquired by the reference electrode, and an output end connected to an output port of the reference electrode module to output a first reference voltage;

a right-leg driving electrode module configured to provide a driving voltage based on a preset right-leg driving electrode of the right-leg driving electrode module, the right-leg driving electrode module comprising a fourth amplifier (U4), which has an input end connected to a second reference voltage, and an output end connected to an output port of the right-leg driving electrode module; and an EEG signal output module configured to receive electrical signals output by the acquisition electrode module, the reference electrode module and the right-leg driving electrode module respectively, calculates, at each moment, a difference between voltage values of the electrical signals output by the acquisition electrode module and the reference electrode module, and a difference between voltage values of the electrical signals output by the acquisition electrode module and the right-leg driving electrode module respectively, and constructs a differential signal as an EEG signal based on the two differences.

7. The multimodal brain function signal acquisition device according to claim 6, wherein the first amplifier (U2) with the input end connected to the output end of the second amplifier (U1) is a feedback circuit amplifier, a capacitor (C2) is connected between an inverted input end and an output end of the feedback circuit amplifier, an end of the capacitor (C2) connected to the inverted input end of the feedback circuit amplifier is further connected to a resistor (R8), and the capacitor (C2) and the resistor (R8) together constitute a feedback circuit of the acquisition electrode module.

8. The multimodal brain function signal acquisition device according to claim 7, wherein the inverted input end of the feedback circuit amplifier is connected to a reference voltage supply end of the acquisition electrode module through the resistor (R8), a non-inverted input end of the feedback circuit amplifier is connected to the reference voltage supply end of the acquisition electrode module through a resistor (R7), a resistor (R3) is connected between the non-inverted input end of the feedback circuit amplifier and the output end of the second amplifier (U1), and a fourth resistor (R5) is connected between the output end of the feedback circuit amplifier and the inverted input end of the second amplifier (U1).

9. The multimodal brain function signal acquisition device according to claim 8, wherein a loop is further disposed between the output end and the inverted input end of the second amplifier (U1), and the loop comprises a fifth resistor (R4), a sixth resistor (R9), a seventh resistor (R6) and a second capacitor (C3), wherein the sixth resistor (R9) and the second capacitor (C3) are connected in parallel, a first end of the fifth resistor (R4) is connected to the output end of the second amplifier (U1), and a second end of the fifth resistor (R4) is connected to a first common end of the sixth resistor (R9) and the second capacitor (C3); a first end of the seventh resistor (R6) is connected to a second common end of the sixth resistor (R9) and the second capacitor (C3), and a second end of the seventh resistor (R6) is connected to one end of the fourth resistor (R5) which is connected to the inverted input end of the second amplifier (U1);

the second common end of the sixth resistor (R9) and the second capacitor (C3) connected in parallel is further connected to the reference voltage supply end of the acquisition electrode module.

10. The multimodal brain function signal acquisition device according to claim 6, wherein an input end of the third amplifier (U3) accesses the electrical signal acquired by the reference electrode through an eighth resistor (R10), and an output end of the third amplifier (U3) outputs the first reference voltage through a ninth resistor (R11).

11. The multimodal brain function signal acquisition device according to claim 6, wherein an inverted input end of the fourth amplifier (U4) is connected to the second reference voltage via a tenth resistor (R13), an output end of the fourth amplifier (U4) is connected to an eleventh resistor (R14), a third capacitor (C5) is connected between the inverted input end of the fourth amplifier (U4) and the output port of the right-leg driving electrode module, and one end of the third capacitor (C5) is connected to one end of the eleventh resistor (R14) outputting an electric signal.

12. The multimodal brain function signal acquisition device according to claim 11, wherein the one end of the third capacitor (C5) is connected to the one end of the eleventh resistor (R14) outputting the electrical signal, and is further connected to the output port of the right-leg driving electrode module.

13. The multimodal brain function signal acquisition device according to claim 9, wherein the reference electrode module further comprises a twelfth resistor (R12) a thirteenth resistor (X1), the thirteenth resistor (X1) is connected between analog ground and the twelfth resistor (R12), and the twelfth resistor (R12) is connected between the thirteenth resistor (X1) and an inverted input end of the third amplifier (U3);

the third resistor (R3), the fourth resistor (R5), the seventh resistor (R6) and the second resistor (R7) in the acquisition electrode module and the twelfth resistor (R12) and the thirteenth resistor (X1) in the reference electrode module satisfy the following formula:

$$X1*R7*R6=R12*(R7*R5+R3*R6+R5*R3);$$

wherein R3, R5, R6, R7, R12 and X1 represent values of the third resistor, the fourth resistor, the seventh resistor, the second resistor, the twelfth resistor and the thirteenth resistor, respectively.

14. The EEG signal acquisition device according to claim 9, wherein a differential gain of the acquisition electrode module is calculated according to the following formula:

$$G=(R5/R6+1)*(R3/R7+1);$$

wherein G represents the differential gain, and R3, R5, R6 and R7 represent values of the third resistor, the fourth resistor, the seventh resistor and the second resistor, respectively.

15. A brain function signal acquisition method using the multimodal brain function signal acquisition device according to claim 1, the method comprising:

obtaining the electroencephalogram (EEG) signal acquired by the EEG signal acquisition device and the current signal acquired by the near infrared signal acquisition device;

inputting the EEG signal acquired by the EEG signal acquisition device into the first analog-digital converter, which converts the EEG signal into the first digital signal and transmits the first digital signal to the micro-control unit;

inputting the current signal into the transimpedance amplifier to convert the current signal into a voltage signal, and inputting the voltage signal into the second analog-to-digital converter, which converts the voltage signal into the second digital signal and transmits the second digital signal to the micro-control unit;

processing the first digital signal and the second digital signal respectively by the micro-control unit to convert the first digital signal and the second digital signal into EEG data and functional near infrared data of the user's brain respectively; and analyzing the EEG data and the functional near infrared data to obtain an activity situation of the user's brain.

16. The brain function signal acquisition method according to claim 15, wherein the first analog-to-digital converter and the second analog-to-digital converter respectively transmit the first digital signal and the second digital signal to the micro-control unit through an SPI protocol.

17. The brain function signal acquisition method according to claim 16, further comprising:

after the micro-control unit converts the first digital signal and the second digital signal into the EEG data and the functional near infrared data of the user's brain, respectively, transmitting the EEG data and the functional near infrared data of the user's brain to a data processing device, so that the EEG data and the functional near infrared data of the user's brain are converted into an EEG and a functional near infrared spectrogram, respectively, by the data processing device.

18. The brain function signal acquisition method according to claim 15, further comprising:

before inputting the EEG signal acquired by the EEG signal acquisition device into the first analog-digital converter, sequentially performing high-pass filtering, low-pass filtering and signal amplitude amplification on the acquired EEG signal, so as to input the amplified EEG signal into the first analog-to-digital converter;

wherein the high-pass filtering filters out the EEG signal with a frequency lower than 0.5 Hz, and the low-pass filtering filters out the EEG signal with a frequency higher than 200 Hz.

19. The brain function signal acquisition method according to claim 15, further comprising:

performing low-pass filtering on the voltage signal before inputting the voltage signal into the second analog-to-digital converter, so as to input the low-pass filtered voltage signal into the second analog-to-digital converter, wherein the low-pass filtering filters out the voltage signal with a frequency higher than 10 Hz.

20. The multimodal brain function signal acquisition device according to claim 1, the first end of the light guide column is fixed on the cap.

* * * * *